United States Patent [19]

Föry et al.

[11] 4,439,230
[45] Mar. 27, 1984

[54] OXIME DERIVATIVES FOR PROTECTING PLANT CROPS

[75] Inventors: Werner Föry, Basel; Henry Martin, Allschwil, both of Switzerland; Georg Pissiotas, Lörrach, Fed. Rep. of Germany

[73] Assignee: Ciba-Geigy Corporation, Ardsley, N.Y.

[21] Appl. No.: 398,166

[22] Filed: Jul. 14, 1982

Related U.S. Application Data

[62] Division of Ser. No. 68,263, Aug. 20, 1979, Pat. No. 4,353,935.

[30] Foreign Application Priority Data

Aug. 31, 1978 [CH] Switzerland .......................... 9201/78

[51] Int. Cl.³ .................... A01N 43/38; C07D 209/48
[52] U.S. Cl. ........................................ 71/96; 548/477; 548/513
[58] Field of Search ...................... 548/477, 513; 71/96

[56] References Cited

U.S. PATENT DOCUMENTS 3,503,732  3/1970  Cahoy ................................... 71/121
3,692,835  9/1972  Van Dijk et al. ............ 260/566 AE
3,803,235  4/1974  Van Dijk et al. ............ 260/566 AE
3,937,841  2/1976  Van Dijk ............................. 424/327
4,192,818  3/1980  Van Dijk et al. ............ 260/566 AE

FOREIGN PATENT DOCUMENTS 2808317  9/1978  Fed. Rep. of Germany .

Primary Examiner—Donald G. Daus
Assistant Examiner—M. C. Eakin
Attorney, Agent, or Firm—Frederick H. Rabin

[57] ABSTRACT

Oxime derivatives of the following formula are described:

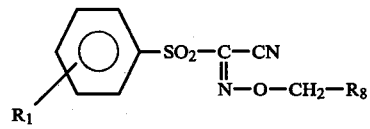

wherein $R_1$ is hydrogen or halogen, and $R_8$ is phthalimido, 4, 5, 6, 7-tetrahydrophthalimido or 3a, 4, 7, 7a-tetrahydrophthalimido attached at the nitrogen atom to the remainder of the molecule. These compounds are used for protecting plant crops from the action of aggressive agricultural chemicals.

3 Claims, No Drawings

OXIME DERIVATIVES FOR PROTECTING PLANT CROPS

This is a division of application Ser. No. 068,263 filed on Aug. 20, 1979 now U.S. Pat. No. 4,353,935.

The present invention relates to a method of protecting plant crops from the phytotoxic action of potent herbicides by means of oxime derivatives and also to a number of novel oxime derivatives.

The oxime derivatives employed as active compounds have the formula I

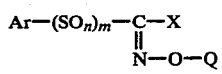

wherein
n is 0, 1 or 2 and m is 0 or 1, and
Ar is a phenyl radical

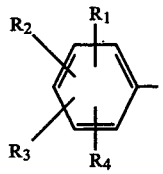

a naphthyl radical substituted by $R_2$ and $R_3$, a 5- to 10-membered heterocyclic radical which contains not more than 3 identical or different heteroatoms N, O and/or S and which is substituted by $R_2$, $R_3$ and $R_4$ and can be substituted by oxo or thiono, or if m is O, Ar is a radical R-CO, wherein R is a radical —$OR_5$, in which $R_5$ is an aliphatic group containing not more than 8 carbon atoms or is an araliphatic group containing not more than 15 carbon atoms or is a cycloaliphatic or aromatic group, each containing not more than 10 carbon atoms, while the possible substituents of the aromatic radicals or of the cycloaliphatic radical are halogen, —CN, —$NO_2$, lower alkyl, lower alkoxy, haloalkyl; or R is a radical —NH—CO—NH—$R_7$ or a radical —N($R_6$)($R_7$), wherein $R_6$ is hydrogen or lower alkyl and $R_7$ is hydrogen or an aliphatic group containing not more than 8 carbon atoms or an araliphatic group containing not more than 15 carbon atoms, or a cycloaliphatic or aromatic group containing not more than 10 carbon atoms, while possible substituents of the aromatic groups or of the cycloaliphatic radical are halogen, —CN, $NO_2$, lower alkyl, lower alkoxy, or haloalkyl; or R is a radical —N($R_6$)($R_7$), wherein $R_6$ and $R_7$ together form a 5- or 6-membered heterocyclic ring which can additionally contain oxygen as possible further heteroatom,
$R_1$ is hydrogen, halogen, lower alkyl, lower alkoxy or a p-phenoxy radical which is unsubstituted or at most disubstituted by halogen, CN, $NO_2$, $CF_3$,
$R_2$, $R_3$ and $R_4$, each independently of the other, are hydrogen, halogen, CN, $NO_2$, lower alkyl, lower alkoxy, haloalkyl, haloalkoxy, lower alkanoyl, OH, phenyl, halophenyl, lower carbalkoxy, lower alkoxycarbonyl, lower alkoxycarbonyloxy, lower carbamoyloxy, lower alkylthio, lower alkylsulfonyl, phenalkoxy, cyclohexyl, $NH_2$ —NH-lower alkyl, —N(di-lower alkyl), lower alkanoylamino, carbamoyl, sulfamoyl,
X is hydrogen, —CN, halogen, lower alkyl, lower alkanoyl, —COOH, a carboxylic acid ester radical, a carbamoyl radical, and
Q is the radical —$C_aH_{2a}$—$R_8$, wherein a is an integer between 1 and 6, while the corresponding radical can also be branched and $R_8$ is one of the following radicals:

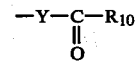

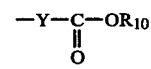

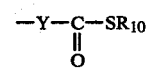

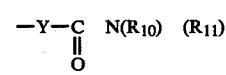

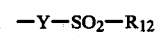

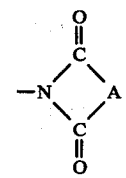

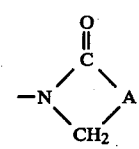

wherein $R_9$ is hydrogen, a cycloaliphatic, araliphatic or aromatic group which is unsubstituted or mono- or polysubstituted at the ring by CN, $NO_2$, halogen, lower alkyl, lower alkoxy or haloalkyl, or is lower alkenyl, lower haloalkenyl or lower alkynyl, $R_{10}$ is an aliphatic group or a cycloaliphatic, araliphatic or aromatic group which is unsubstituted or mono- or polysubstituted at the ring by CN, $NO_2$, halogen, lower alkyl, lower alkoxy or haloalkyl, $R_{11}$ is hydrogen, lower alkyl or cycloalkyl, $R_{12}$ is lower alkyl or an aromatic group, while Y is O, S, SO, $SO_2$ or

and
A is $C_2$-$C_3$alkylene or $C_2$-$C_3$alkenylene which is unsubstituted or substituted by halogen, CN or lower alkyl and which together with a carbon chain which is unsubstituted or substituted by halogen, CN or lower alkyl can form a fused ring, and Hal is halogen.

By halogen in formula I is meant fluorine, chlorine, bromine or iodine.

Carboxylic acid esters are lower alkyl esters, Carbamoyl radicals, in addition to —CONH$_2$, are also monoalkyl-substituted or symmetrically or unsymmetrically dialkyl-substituted amides, while the alkyl groups are lower alkyl groups.

The term alkyl by itself or as moiety of another substituent comprises branched or unbranched alkyl groups of 1 to 8 carbon atoms. Lower alkyl by itself or as moiety of another substituent denotes $C_1$–$C_4$alkyl. Examples are methyl, ethyl, propyl, isopropyl, butyl, isobutyl, sec-butyl, tert-butyl, as well as the higher homologues amyl, isoamyl, hexyl, heptyl, octyl, together with their isomers. By analogy, alkanoyl or cyanoalkyl groups contain an additional carbon atom. Lower alkenyl or alkynyl groups accordingly contain not more than 4 carbon atoms.

The term "aliphatic group" comprises saturated radicals (alkyls), and unsaturated radicals (alkenyls, alkadienyls, alkynyls), halogen-substituted radicals, cyano-substituted radicals, and radicals which are interrupted by oxygen. These radicals contain not more than 8 carbon atoms.

The term "aromatic group" comprises phenyl and naphthyl, which can in principle be mono- or polysubstituted by CN, NO$_2$, halogen, lower alkyl, lower alkoxy or haloalkyl. An araliphatic radical comprises an unsubstituted or mono- to trisubstituted phenyl or naphthyl radical which is bonded through lower alkyl or lower alkenyl to the radical of the molecule. Examples are benzyl, phenethyl, phenylallyl and their homologues.

Unsubstituted or substituted heterocyclic radicals can be mono- or bicyclic. Examples are: furan, nitrofuran, bromofuran, methylfuran, thiophene, chlorothiophene, pyridine, 2,6-dichloropyridine, pyrimidine, pyridazine, pyrazine, piperidine, methylpiperidine, morpholine, thiomorpholine, tetrahydrofurane, oxazole, pyrazole, pyrrole, pyrroline, pyrrolidine, thiazole, 2,3-dihydro-4H-pyrane, pyrane, dioxane or 1,4-oxathi-(2)-ine, benzthiazole, benzoxazole, benzimidazole, quinoline, benz-1,3-dioxolane. Cycloalkyl groups are cyclopropyl, cyclobutyl, cyclopentyl, cyclohexyl and cycloheptyl. Cycloaliphatic radicals correspond to these ring systems, but, where possible, can additionally contain one or more double bonds.

The compounds of the formula I can be obtained
(a) with the exception of compounds, wherein Q is —C≡C Hal, by reacting a compound of the formula II

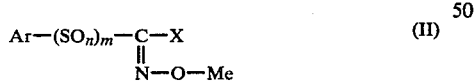   (II)

with a compound of the formula III

Hal'-Q   (III)

or
(b) where Q is —C≡C Hal, by reacting a compound of the formula IV

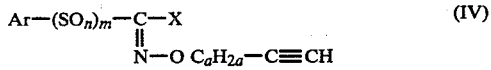   (IV)

with halogen in the presence of a base. In the above formulae II, III and IV, Ar, X, Q, m and n are as defined for formula I, Hal' is halogen, preferably chlorine or bromine, and Me is hydrogen or a metal cation, preferably an alkali metal or alkaline earth metal cation.

The compounds of the formula IV can be obtained by a process analogous to that of process (a).

The reactions can be carried out in the presence or absence of solvents which are inert to the reactants. Examples of suitable solvents are: alcohols, such as ethanol; ketones, such as aceton; nitriles, such as acetonitrile; N,N-dialkylated amides, such as dimethyl formamide; dimethyl sulfoxide, pyridine, or, in process (b), also water as well as mixtures of these solvents with one another.

Where Me is hydrogen, the process is carried out in the presence of a base. Examples of suitable bases are inorganic bases, such as the oxides, hydroxides, hydrides, carbonates and bicarbonates of alkali metals and alkaline earth metals, as well as e.g. tertiary amines, such as trialkylamines (e.g. triethylamine), and pyridine. The reaction temperatures are in the range between 0° and 150° C. The reactions are carried out under normal pressure and, in (a), optionally in a nitrogen atmosphere.

The compounds of the formula II are prepared by methods analogous to known ones. Processes (a) and (b) also constitute an object of the invention.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

The content of active substance in commercial compositions is between 0.1% and 90% by weight.

For application, the compounds of the formula I may be processed to the following formulations (in which the percentages by weight in brackets refer to advantageous amounts of active ingredient):

Solid Formulations dusts, tracking agents, (up to 10%) granules (coated granules, impregnated granules and homogeneous granules); pellets (1 to 80%);

Liquid Formulations (a) active substance concentrates which are dispersible in water: wettable powders, pastes; (25–90% in commercial packs, 0.01 to 15% in ready for use solutions; emulsifiable concentrates and concentrated solutions (10 to 50%; 0.01 to 15% in ready for use solutions).

(b) Solutions (0.1 to 20%); aerosols.

Such compositions also constitute an object of the invention.

Different compounds which are able to antagonise the harmful action of a herbicide on cultivated plants specifically have already been proposed as antidotes, i.e. compounds which protect cultivated plants without noticeably influencing the herbicidal action on the weeds which it is desired to control. Depending on their properties, such antidotes, also known as safeners, can be used for pretreating the seeds of the cultivated plants (dressing seeds or seedlings) or before sowing seeds in furrows or as tank mixture, by themselves or together with the herbicide or after emergence of the plants. The pre-emergence treatment includes both treatment of the crop area before sowing (ppi=pre-plant incorporation)

and treatment of the crop areas after sowing but before emergence of the plants.

Thus, British patent specification No. 1 277 557 discloses the treatment of seed and seedlings of wheat and sorghum with certain esters and amides of oxamic acid before attack by N-methoxymethyl-2'-6'-diethylchloroacetanilide (Alachlor). Other publications (German Offenlegungsschriften Nos. 1 952 910 and 2 245 471, and French patent specification No. 2 021 611), propose antidotes for the treatment of cereals, maize seeds and rice seeds to protect them against attack by herbicidal thiolcarbamates. In German patent specification No. 1 576 676 and U.S. Pat. No. 3 131 509, hydroxyamino-acetanilides and hydantoins are suggested for protecting cereal seeds against carbamates, such as IPC, CIPC, etc.

The further development, however, has shown all these preparations to be unsatisfactory.

Surprisingly, oximes of the formula I have the property of protecting cultivated plants from attack by aggressive agricultural chemicals, in particular herbicides, of the most diverse compound classes, including 1,3,5-triazines, 1,2,4-triazinones, phenylurea derivatives, carbamates, thiolcarbamates, phenoxyacetates, phenoxypropionates, haloacetanilides, halophenoxyacetates, substituted phenoxyphenoxyphenoxyacetates and -propionates, benzoic acid derivatives, where these compounds are not tolerated or insufficiently tolerated by plants.

The rates of application of the antidote with respect to the herbicide depend largely the mode of application. Where a field treatment is carried out, the ratio of antidote of the formula I to phytotoxic chemical is 1:100 to 5:1, preferably 1:20 to 1:1. When dressing seeds and taking similar specific protective measures, however, much lower amounts of antidote are required in comparison with e.g. the amounts of herbicide later employed per hectare of crop area (e.g. about 1:3000 to 1:1000). As a rule, protective measures such as seed dressing with an antidote of the formula I and possible later field treatment with agricultural chemicals are only loosely connected. Pretreated seeds and plants can later come into contact with different chemicals in agriculture, horticulture and forestry.

Accordingly, the invention relates to plant protection compositions which contain, as active ingredient, solely an antidote of the formula I together with conventional carriers. If appropriate or desired, such compositions can additionally be mixed with the chemical against the action of which it is desired to protect the cultivated plant, for example with a herbicide.

Cultivated plants within the scope of this invention are all plants which, in any form, can be harvested (seeds, roots, stalks, tubers, leaves, blossoms) and from which extracts can be obtained (oils, sugar, starch, protein) and which for this purpose are cultivated and tended. To these plants belong e.g. all species of cereals, maize, rice, millet, soybeans, beans, peas, potatoes, vegetables, cotton, sugar beet, sugar cane, ground nuts, tobacco, hops, and also ornamentals, fruit trees and bananas, cocoa and natural rubber plants.

In principle, an antidote can be employed wherever it is desired to protect a cultivated plant from the phytotoxicity of a chemical.

The invention also relates to a method of protecting cultivated plants from aggressive (phytotoxic) chemicals, which comprises applying an oxime derivative of the formula I which acts as antidote, optionally before or after application of the chemical, or also simultaneously with the chemical.

The invention also relates to the propagation products of such cultivated plants which are given a protective treatment with an oxime derivative of the formula I. By propagation products are meant all generative parts of plants which can be used for the propagation of the cultivated plant, for example grains (seeds in the narrow sense), roots, fruit, tubers, rhizomes, parts of stalks, branches (seedlings) and other parts of plants. Propagation products also include pregerminated plants and young plants which, after pregermination or emergence, will be further transplanted. Such young plants can be selectively protected by means of a complete or partial immersion treatment before transplantation.

The following types of substituent or combinations thereof with one another are preferred:

for Q:

(a) $CH_2-C\equiv Cl$ (b) $CH_2$-O-phenyl (unsubstituted or substituted)

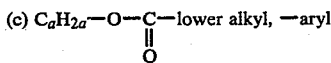

(c) $C_aH_{2a}$—O—C—lower alkyl, —aryl
        ‖
        O

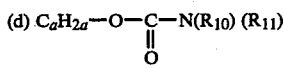

(d) $C_aH_{2a}$—O—C—N($R_{10}$) ($R_{11}$)
        ‖
        O

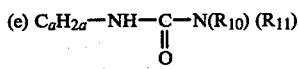

(e) $C_aH_{2a}$—NH—C—N($R_{10}$) ($R_{11}$)
         ‖
         O (f) $C_2H_{2a}$-O-$SO_2$-lower alkyl

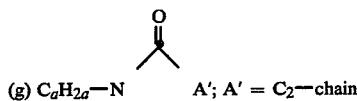

(g) $C_aH_{2a}$—N     A'; A' = $C_2$—chain

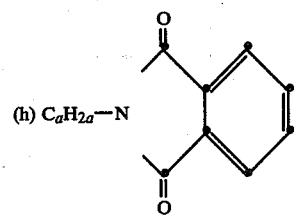

(h) $C_aH_{2a}$—N

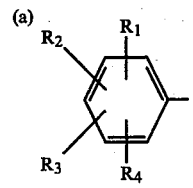

(a)

for Ar:

(b) 1-naphthyl

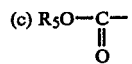

(c) $R_5O$—C—
         ‖
         O (d) benzoxazole (e) benzthiazole for X:
(a) cyano
(b) hydrogen
(c) a carboxylic acid ester radical
(d) lower alkyl
for n and m:
(a) n=2 m=1
(b) m=O The invention is illustrated by the following Examples, but without any restriction to what is described therein. Temperatures are in degrees centigrade, pressures in millibars, and parts and percentages are by weight.

PREPARATIVE EXAMPLES

EXAMPLE 1: Manufacture of

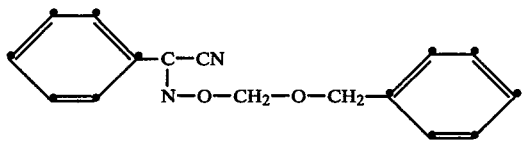

8.4 g (0.05 mole) of the sodium salt of α-phenylacetonitrile oxime were dissolved in 50 ml of dimethyl formamide. With stirring, 7.8 g of chloromethylbenzyl ether were added to this solution at room temperature. After it had been stirred for 8 hours, the reaction mixture was washed with water and extracted with ethyl acetate. The ethyl acetate solution was dried over sodium sulfate and concentrated in vacuo, affording the oily product of the above formula; $n_D^{22}$ 1.5621.

EXAMPLE 2:

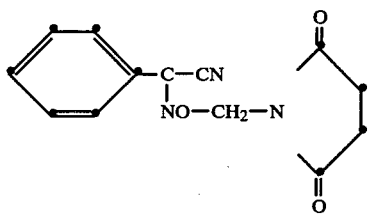

A mixture of 6 g of the sodium salt of α-phenylacetonitrile oxime and 5.5 g of N-chloromethyl-succinimide in 30 ml of dimethyl formamide was stirred under nitrogen for 17 hours at 50° C. The reaction mixture was diluted with ethyl acetate, washed with water, dried and concentrated, affording 9.4 g of a crystalline product with a melting point of 135°-138° C. (Recrystallisation from chloroform/petroleum ether).

EXAMPLE 3: Manufacture of

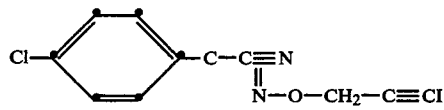

23 g of α-phenylacetonitrile propargyloxime was dissolved in 150 ml of methanol. With stirring and cooling with ice water, 29.5 g of iodine in 100 ml of sodium hydroxide were added in portions at 5° to 10° C. in the course of 30 minutes. When the addition was complete, the reaction mixture was stirred for 4 hours at 5° to 10° C. The suspension was then filtered by suction and the filter cake was washed with water and dried in vacuo at 40°-50° C., affording 33.5 g of the final product with a melting point of 84°-85° C.

The following compounds of the formula (I) can be obtained in analogous manner or by one of the methods described herein.

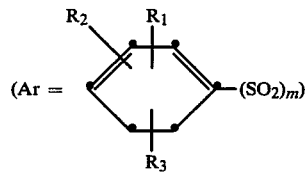

| Compound | $R_1$ | $R_2$ | $R_3$ | m | X | Q | Physical data (°C.) |
|---|---|---|---|---|---|---|---|
| 1 | H | H | H | 0 | CN | $CH_2C{\equiv}Cl$ | m.p. 83–85° |
| 2 | H | 4-Br | H | 0 | CN | $CH_2C{\equiv}Cl$ | oil |
| 3 | 3-Cl | 4-Cl | H | 0 | CN | $CH_2C{\equiv}Cl$ | m.p. 77–79° |
| 4 | 2-Cl | 4-Cl | H | 0 | CN | $CH_2C{\equiv}Cl$ | m.p. 92–95° |
| 5 | H | 4-$CH_3O$ | H | 0 | CN | $CH_2C{\equiv}Cl$ | m.p. 132–134° |
| 6 | H | 4-$CH_3$ | H | 0 | CN | $CH_2C{\equiv}Cl$ | m.p. 98–100° |
| 7 | 3-$CH_3$ | 4 $CH_3$ | H | 0 | CN | $CH_2C{\equiv}Cl$ | m.p. 77–79° |
| 8 | H | 4-Cl | H | 0 | CN | $CH_2C{\equiv}Cl$ | m.p. 84–85° |
| 9 | H | H | H | 0 | CN | 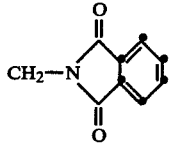 | m.p. 174–178° |

-continued

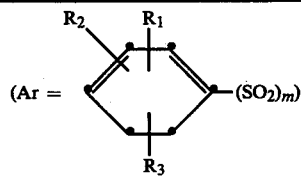

| Compound | R₁ | R₂ | R₃ | m | X | Q | Physical data (°C.) |
|---|---|---|---|---|---|---|---|
| 10 | H | H | H | 0 | CN | CH₂—N(dichloromaleimide) | |
| 11 | H | H | H | 0 | COOCH₃ | CH₂—N(maleimide) | |
| 12 | H | H | H | 0 | COOCH₃ | CH₂—N(tetrahydrophthalimide) | |
| 13 | H | H | H | 0 | CH₃ | CH₂—N(tetrahydrophthalimide) | |
| 14 | H | H | H | 0 | CN | CH₂CH₂—N(succinimide) | |
| 15 | H | 4-Cl | H | 0 | CN | CH₂—N(tetrahydrophthalimide) | |
| 16 | 3-Cl | 4-Cl | H | 0 | CN | CH₂—N(tetrahydrophthalimide) | |
| 17 | H | 4-(t)-C₄H₉ | H | 0 | CN | CH₂—N(dichloromaleimide) | |
| 18 | H | 4-CH₃O | H | 0 | CN | CH₂—N(tetrahydrophthalimide) | |

-continued

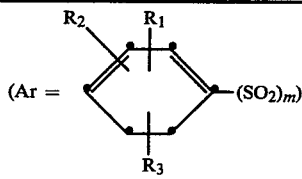

$$(Ar = \text{phenyl ring with } R_1, R_2, R_3 \text{ and } (SO_2)_m)$$

| Compound | R₁ | R₂ | R₃ | m | X | Q | Physical data (°C.) |
|---|---|---|---|---|---|---|---|
| 19 | 3-CH₃ | 4-CH₃ | H | 0 | CN | 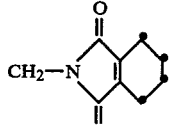 | |
| 20 | H | 4-Cl | H | 0 | CN | 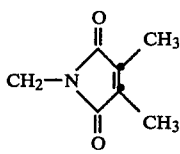 | |
| 21 | 2-Cl | 4-Cl | H | 0 | CN | CH₂—O—CH₂—C₆H₅ | $n_D^{22}$ 1.5745 |
| 22 | H | H | H | 0 | CN | CH₂—O—CH₂—C₆H₅ | $n_D^{22}$ 1.5621 |
| 23 | 2-Cl | 4-Cl | H | 0 | CN | CH₂—CH₂—O—CH—CH₂ | $n_D^{38}$ 1.5510 |
| 24 | H | H | H | 0 | CN | CH₂—CH₂—O—CH—CH₂ | $n_D^{23}$ 1.5362 |
| 25 | H | 4-OC₆H₄F₃(4') | H | 0 | CN | CH₂—O—CH₂—C₆H₅ | |
| 26 | H | H | H | 1 | CN | CH₂—C≡Cl | |
| 27 | H | 4-CH₃ | H | 1 | CN | CH₂—C≡Cl | |
| 28 | H | 4-Cl | H | 1 | CN | CH₂—C≡Cl | |
| 29 | 3-Cl | 4-Cl | H | 1 | CN | CH₂—C≡Cl | |
| 30 | H | 4-CH₃O | H | 1 | CN | CH₂—C≡Cl | |
| 31 | H | 2-Cl | H | 1 | CN | CH₂—C≡Cl | |
| 32 | 2-Cl | 4-Cl | H | 1 | CN | CH₂C≡Cl | |
| 33 | 3-Cl | 4-Cl | H | 1 | COOCH₃ | CH₂—C≡Cl | |
| 34 | 4-Cl | H | H | 1 | COOCH₃ | CH₂—C≡Cl | |
| 35 | H | H | H | 1 | COOCH₃ | CH₂—C≡Cl | |
| 36 | H | H | H | 1 | COOC₂H₅ | CH₂—C≡Cl | |
| 37 | H | H | H | 0 | CN | CH₂—CH₂—OH | m.p. 56° |
| 38 | 2-Cl | 4-Cl | H | 0 | CN | CH₂—CH₂—OH | $n_D^{26}$ 1.6181 |
| 39 | H | 4-Cl | H | 0 | CN | CH₂—CH₂—OH | m.p. 50° |
| 40 | H | H | H | 0 | CN | —CH₂CH₂OCONHC₆H₃Cl₂(3,4) | m.p. 77–78° |
| 41 | H | H | H | 0 | CN | CH₂CH₂OCONHC₆H₄CF₃(3) | $n_D^{20}$ = 1.5434 |
| 42 | H | H | H | 0 | CN | CH₂CH₂OCONHC₆H₄Cl(4) | m.p. 94–95° |
| 43 | H | H | H | 0 | CN | CH₂CH₂OCONHC₆H₅ | m.p. 71–72° |
| 44 | H | H | H | 0 | CN | CH₂CH₂OCONHCH₃ | m.p. 57–58° |
| 45 | H | H | H | 0 | CN | CH₂CH₂OCOC₂H₅ | $n_D^{26}$ = 1.5297 |
| 46 | H | H | H | 0 | CN | CH₂CH₂OCOCH₃ | $n_D^{26}$ 1.5322 |
| 47 | H | H | H | 0 | CN | CH₂CH₂OCOCH₂Cl | $n_D^{25}$ 1.5455 |
| 48 | H | H | H | 0 | H | CH₂CH₂OCOC₆H₅ | $n_D^{22}$ = 1.5745 |
| 49 | 2-Cl | 4-Cl | H | 0 | H | CH₂—C≡Cl | m.p. 92–94° |
| 50 | 2-Cl | 6-Cl | H | 0 | H | CH₂—C≡Cl | m.p. 83–84° |
| 51 | 3-Cl | 4-Cl | H | 0 | H | CH₂—C≡Cl | m.p. 83–84° |
| 52 | H | 3-NO₂ | H | 0 | H | CH₂—C≡Cl | m.p. 113–114° |
| 53 | H | 4-NO₂ | H | 0 | H | CH₂—C≡Cl | m.p. 198–199° |
| 54 | H | 4-CN | H | 0 | COOCH₃ | CH₂—CH₂—O—C₆H₅ | |
| 55 | H | 4-CN | H | 0 | CH₃ | CH₂—CH₂—OCONHCH₃ | |
| 56 | H | 4-CN | H | 0 | CN | CH₂—CH₂—OCONHCH₃ | |
| 57 | H | 4-CN | H | 0 | CN | CH₂—CH₂—OCOCH₃ | |
| 58 | H | 2-CN | H | 0 | CN | CH₂—CH₂—OCOCH₃ | |
| 59 | H | 4-NO₂ | H | 0 | CH₃ | CH₂—C≡Cl | |
| 60 | H | 4-NO₂ | H | 0 | CN | CH₂—C≡Cl | |
| 61 | H | 2-CH₃ | 4-OCONHCH₃ | 0 | CH₃ | CH₂—CH₂—O—CONHCH₃ | |
| 62 | 3-OCH₃ | 2-NO₂ | 4-OCOCH₃ | 0 | CN | 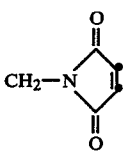 | |
| 63 | 3-Cl | 2-OCOCH₃ | 5-Cl | 0 | CH₃ | CH₂—O—C₆H₅ | |
| 64 | 4-CH₃ | 2-OCOCH₃ | 6-CH₃ | 0 | H | CH₂CH₂—NHCO—C₆H₅ | |
| 65 | H | 4-N(C₂H₅)₂ | H | 0 | CH₃ | CH₂CH₂—NHCOCH₃ | |
| 66 | 3-CH₃ | 5-CH₃ | H | 0 | CH₃ | CH₂CH₂—OCH₂C₆H₃Cl₂(2,4) | |
| 67 | H | 4-Cyclo- | H | 0 | H | CH₂CH₂—OH | |

-continued

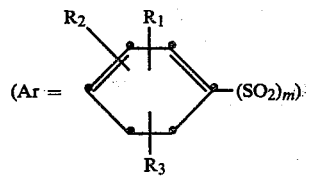

| Compound | R₁ | R₂ | R₃ | m | X | Q | Physical data (°C.) |
|---|---|---|---|---|---|---|---|
| 68 | H | hexyl 4-Br | H | 0 | CONHCH₃ | CH₂CH₂—S—CH₂—C₆H₅ | |
| 69 | H | 2-OCH₂C₆H₅ | H | 0 | CH₃ | —CH₂—N(CH₂CH₂)C=O (azetidinone) | |
| 70 | H | 4-C₆H₄Br(4) | H | 0 | CH₃ | —CH₂—N(CO)C(CH₃)₂(CO) succinimide dimethyl | |
| 71 | H | 4-OCH₂C₆H₅ | H | 0 | CH₃ | CH(CH₃)—NHCOCH₃ | |
| 72 | H | 4-CH=CHC₆H₅ | H | 0 | CH₃ | CH(CH₃)CH₂—NCHO | |
| 73 | 3-Cl | 2-OCOCH₃ | 6-Cl | 0 | C₂H₅ | —CH₂—N(methyl azetidinone) | |
| 74 | 3-Cl | 2-OCOCH₃ | 6-Cl | 0 | CH₃ | CH₂CH₂—OCOCH₂Cl | |
| 75 | 5-Cl | 2-OCONHCH₃ | H | 0 | CH₃ | CH₂—CH₂N(CH₃)CO—furyl-(2) | |
| 76 | H | 4-CH₃O | H | 0 | CN | CH₂OCH₂C₆H₅ | $n_D^{24}$ 1.5785 |
| 77 | H | 4-CH₃ | H | 0 | CN | CH₂OCH₂C₆H₅ | $n_D^{24}$ 1.5655 |
| 78 | H | 4-CH₃ | H | 0 | CN | C₂H₄OCH=CH₂ | $n_D^{24}$ 1.5159 |
| 79 | H | 4-Cl | H | 0 | CN | C₂H₄OCH=CH₂ | m.p. 41–43° |
| 80 | H | H | H | 0 | CN | CH(CH₃)CH₂OH | $n_D^{25}$ 1.5492 |
| 81 | H | H | H | 0 | CN | CH₂SCH₂C₆H₅ | $n_D^{25}$ 1.5952 |
| 82 | H | 4-Cl | H | 0 | CN | CH₂OCH₂C₆H₅ | $n_D^{23}$ 1.5604 |
| 83 | H | 4-Cl | H | 0 | CN | C₂H₄OCH₂C₆H₅ | m.p. 74–75° |
| 84 | H | H | H | 0 | CN | —C₂H₄—OC₆H₅ | m.p. 70–71° |
| 85 | H | 4-CH₃ | H | 0 | CN | —C₂H₄—OC₆H₅ | m.p. 84–85° |
| 86 | H | 4-OCH₃ | H | 0 | CN | —C₂H₄—OC₆H₅ | m.p. 76–77° |
| 87 | H | 4-OCH₃ | H | 0 | CN | —C₂H₄—O—CH=CH₂ | m.p. 57–58° |
| 88 | H | 4-OCH₃ | H | 0 | CN | —CH(CH₃)—CH₂—OH | $n_D^{24}$ = 1.5379 |
| 89 | H | H | H | 1 | CN | —CH₂—N (tetrahydroisoquinoline-1,3-dione) | $n_D^{26}$: 1.5498 |
| 90 | H | H | H | 1 | CN | —CH₂—N (hexahydroisoquinoline dione with alkene) | $n_D^{26}$: 1.5452 |
| 91 | H | H | H | 1 | CN | —CH₂—N (maleimide-type) | $n_D^{26}$: 1.5176 |

-continued

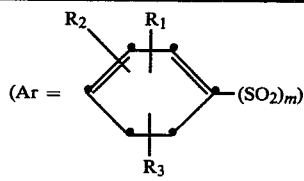

| Compound | R₁ | R₂ | R₃ | m | X | Q | Physical data (°C.) |
|---|---|---|---|---|---|---|---|
| 92 | H | H | H | 1 | CN | -CH₂-N(isoquinoline-1,3-dione) | m.p. 95–7° C. |
| 93 | H | 4-Cl | H | 1 | CN | -CH₂-N(maleimide) | |
| 94 | H | H | H | 1 | CN | -CH₂-N(phthalimide) | m.p. 120–2° C. |
| 95 | H | H | H | 1 | CN | -CH₂-N(tetrahydroisoquinoline-1,3-dione) | m.p. 98–100° C. |
| 96 | H | 4-CH₃ | H | 1 | CN | -CH₂-N(maleimide) | |
| 97 | H | H | H | 1 | CN | -CH₂-N(isoquinoline-1,3-dione) | m.p. 135–7° C. |
| 98 | H | H | H | 1 | CN | -CH₂-N(hexahydroisoquinoline-1,3-dione) | $n_D^{26}$: 1.5486 |
| 99 | H | H | H | 1 | CN | -CH₂-N(tetrahydroisoquinoline-1,3-dione) | $n_D^{25}$: 1.5515 |
| 100 | H | 4-Cl | H | 1 | CN | -CH₂-N(tetrahydroisoquinoline-1,3-dione) | $n_D^{26}$ = 1.5376 |
| 101 | H | H | 4-Cl | 0 | CN | -CH₂-N(phthalazine N-oxide) | m.p. 152–3° |

-continued

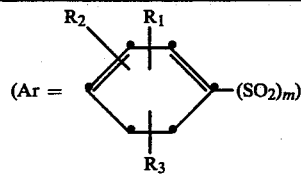

| Compound | R₁ | R₂ | R₃ | m | X | Q | Physical data (°C.) |
|---|---|---|---|---|---|---|---|
| 102 | H | H | H | 0 | CN | —CH₂—N(phthalimide) | m.p. 146–8° |
| 103 | H | H | H | 0 | CN | —CH₂—N(tetrahydrophthalimide) | m.p. 105-6° |
| 104 | H | 4-Cl | H | 0 | CN | —CH₂—N(2-oxopiperidinyl) | m.p. 98–99° |
| 105 | 2-Cl | 4-Cl | H | 0 | H | CH₂—C≡Cl | m.p. 92–94° |
| 106 | 2-Cl | H | 6-Cl | 0 | H | CH₂—C≡Cl | m.p. 83–84° |
| 107 | H | 3-NO₂ | H | 0 | H | CH₂—C≡Cl | m.p. 113–114° |
| 108 | 3-Cl | 4-Cl | H | 0 | H | CH₂—C≡Cl | m.p. 83–4° |
| 109 | H | 4-CH₃ | H | 0 | CN | CH₂OCH₂—C₆H₄—CH₃ | |
| 110 | H | 4-OCH₃ | H | 0 | CN | CH₂OCH₂—C₆H₄—CH₃ | |
| 111 | 2-Cl | 4-Cl | H | 0 | CN | CH₂OCH₂C₆H₅ | |
| 112 | 3-Cl | 4-Cl | H | 0 | CN | CH₂OCH₂C₆H₅ | |
| 113 | H | 4-CH₃ | H | 0 | CN | CH₂OCH₂—C₆H₄—OCH₃ | |
| 114 | H | 4-CH₃ | H | 0 | CN | CH₂OCH₂—C₆H₄—Cl | |
| 115 | 2-OCH₃ | H | H | 0 | CN | CH₂OCH₂C₆H₅ | |
| 116 | H | 3-CH₃ | H | 0 | CN | CH₂OCH₂C₆H₅ | |
| 117 | H | 3-Cl | H | 0 | CN | CH₂OCH₂C₆H₅ | |
| 118 | H | 3-CN | H | 0 | CN | CH₂OCH₂C₆H₅ | |
| 119 | H | 3-CF₃ | H | 0 | CN | CH₂OCH₂C₆H₅ | |
| 120 | H | 4-Br | H | 0 | CN | CH₂OCH₂C₆H₅ | |
| 121 | H | 4-F | H | 0 | CN | CH₂OCH₂C₆H₅ | |
| 122 | H | 3-OCH₃ | H | 0 | CN | CH₂OCH₂—C₆H₄—CH₃ | |
| 123 | 3-Cl | 4-CH₃ | H | 0 | CN | CH₂OCH₂C₆H₅ | |
| 124 | H | H | H | 1 | CN | CH₂OCH₂C₆H₅ | |
| 125 | H | 4-CH₃ | H | 1 | CN | CH₂OCH₂C₆H₅ | |
| 126 | H | 4-Cl | H | 1 | CN | CH₂OCH₂C₆H₅ | |
| 127 | H | 4-CH₃ | H | 0 | CH₃ | CH₂OCH₂C₆H₅ | |
| 128 | H | 4-OCH₃ | H | 0 | CH₃ | CH₂OCH₂C₆H₅ | |
| 129 | H | 4-Cl | H | 0 | CH₃ | CH₂OCH₂C₆H₅ | |
| 130 | H | 4-CH₃ | H | 0 | H | CH₂OCH₂C₆H₅ | |
| 131 | H | 4-OCH₃ | H | 0 | H | CH₂OCH₂C₆H₅ | |
| 132 | 3-Cl | 4-Cl | H | 0 | H | CH₂OCH₂C₆H₅ | |

TABLE II (Ar = 1-naphth 1; m = 0)

| Compound | X | Q | Physical data (°C.) |
|---|---|---|---|
| 133 | CN | CH$_2$CH$_2$OH | $n_D^{26}$ 1.6172 |
| 134 | CN | CH$_2$–N(succinimide) | m.p. 166–8° |
| 135 | CN | CH$_2$CH$_2$–N(3,4-dichloromaleimide) | |
| 136 | CN | CH$_2$OCH$_2$C$_6$H$_5$ | $n_D^{22}$ 1.6300 |
| 137 | CN | CH$_2$CH$_2$OCH=CH$_2$ | $n_D^{32}$ 1.5918 |
| 138 | CN | –CH$_2$–N(phthalimide) | m.p. 145–146° |

TABLE III (Ar = pyridyl; m = 0; X = H)

| Compound | Z | Q |
|---|---|---|
| 139 | S | CH$_2$–CH$_2$–NH–CO–NH–CH$_3$ |
| 140 | S | CH$_2$–CH$_2$–NH–CO–NH–C$_6$H$_4$Cl(4) |
| 141 | S | CH$_2$–CH$_2$–O–CO–NH–C$_6$H$_3$Cl$_2$(3,4) |
| 142 | S | CH(CH$_3$)–CH$_2$–O–C$_6$H$_3$–NO$_2$(2)-CF$_3$(4) |
| 143 | O | CH$_2$–C≡Cl |
| 144 | O | CH$_2$–N(2,3-dichloromaleimide) |
| 145 | O | CH$_2$–CH$_2$–N(CH$_3$)–CO–C$_2$H$_5$ |
| 146 | O | CH$_2$–CH$_2$–O–C$_6$H$_3$–NO$_2$(2)–CF$_3$(4) |

TABLE IV (Ar = substituted pyridyl; m = 0)

$$-\underset{\underset{NO-Q}{\|}}{C}-X$$

| Compound | R$_{20}$ | R$_{21}$ | (–C(X)=NO–Q substituent) |
|---|---|---|---|
| 147 | 2-Cl | 6-Cl | 4-CH=NO–CH$_2$–CH$_2$N(CH$_3$)$_2$ |
| 148 | H | H | 4-C(CH$_3$)=NO–CH$_2$–N(pyrroledione) |
| 149 | H | H | 2-CH=NO–CH$_2$–O–C$_6$H$_5$ |
| 150 | H | H | 3-C(CH$_3$)=NO–CH$_2$–CH$_2$–O–C$_6$H$_5$Cl$_2$(2,4) |
| 151 | H | H | 4-C(CN)=NO–CH$_2$–N(pyrroledione) |
| 152 | H | H | 3-C(CH$_3$)=NO–CH$_2$–O–C$_6$H$_5$ |
| 153 | H | H | 3-C(COOCH$_3$)=NO–CH$_2$–O–C$_6$H$_5$ |
| 154 | H | H | CH$_2$–C≡CH    m.p. 26° |

TABLE V $$(Ar = \text{benzo-fused ring with } R_{22}, R_{23}, Z_1, N; \ m = 0)$$

| Compound | $Z_1$ | $R_{22}$ | $R_{23}$ | X | Q |
|---|---|---|---|---|---|
| 155 | O | H | H | CN | $CH_2$–N(3,4-dichloro-2,5-dioxopyrrolin-1-yl) |
| 156 | O | H | H | CN | $CH_2$–N(3,4-dimethyl-2,5-dioxopyrrolin-1-yl) |
| 157 | O | H | H | H | $CH_2$–$CH_2$–O–CO–NH–$CH_3$ |
| 158 | O | H | $CH_3$ | CN | $CH_2$–N(2,5-dioxopyrrolin-1-yl) (maleimidomethyl) |
| 159 | O | Cl | H | CN | $CH_2$–$CH_2$–$CH_2$–O–CON($CH_3$)$_2$ |
| 160 | S | H | H | CN | $CH_2$–$CH_2$–O–$C_6H_5$ |
| 161 | S | H | H | Cl | $CH_2$–N(2,5-dioxopyrrolin-1-yl) |
| 162 | S | H | H | CN | $CH_2$–$CH_2$–O–CO–NH–$CH_3$ |
| 163 | S | H | $CH_3$ | $CH_3$ | $CH_2$–$CH_2$–O–CO–$CH_3$ |
| 164 | S | H | –$NO_2$ | $CH_3$ | $CH_2$–$CH_2$–OH |
| 165 | N–$CH_3$ | H | H | CN | CH–C≡Cl |
| 166 | N–$CH_3$ | H | H | CN | $CH_2$–N(3,4-dimethyl-2,5-dioxopyrrolin-1-yl) |
| 167 | N–$CH_3$ | H | H | CN | $CH_2$–O–$C_6H_5$ |
| 168 | N–$CH_3$ | $CH_3$ | H | CN | $CH_2$–N(3,4-dimethyl-2,5-dioxopyrrolin-1-yl) |
| 169 | N–$CH_3$ | Cl | H | $CH_3$ | $CH_2$–O–$C_6H_5$ |

TABLE VI

Ar = [phenyl-N=N-C(R24)=C(CH3)-N pyrazole ring]; X = H; m = O

| Compound | R24 | Q |
|---|---|---|
| 170 | H | CH2-N(succinimide) |
| 171 | CH3 | CH2—O—C6H5 |
| 172 | H | CH2—O—C6H5 |

TABLE VII (Ar = naphthyl with R25, R26, Cl substituents); X = H; m = O

| Compound | Z2 | R25 | R26 | Q |
|---|---|---|---|---|
| 173 | O | H | Cl | CH2—C≡Cl |
| 174 | O | H | Cl | CH2—CH2—OH |
| 175 | O | Cl | H | CH2—CH2—O—CO—NH—CH3 |
| 176 | O | Cl | Cl | CH2—C≡Cl |
| 177 | O | H | H | CH2—C≡Cl |
| 178 | S | H | Cl | CH2-N(maleimide) |
| 179 | S | Cl | Cl | CH2—CH2—O—CO—NH—C6H4Cl(4) |
| 180 | S | H | Cl | CH2—CH2—OH |

TABLE VIII

Ar = quinoline with R27; X = CH3; m = O

| Compound | R27 | Q |
|---|---|---|
| 181 | O—CO—CH3 | CH2—O—C6H5 |
| 182 | O—CO—CH3 | CH2—O—C6H4Cl(4) |
| 183 | O—CO—NH—CH3 | CH2—O—C6H5 |
| 184 | O—CO—C2H5 | CH2—O—C6H4(NO2) |
| 185 | O—CO—CH2—Cl | 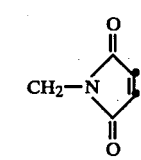 |
| 186 | O—CO—NH—C2H5 | CH2—CH2—O—C6H3—Cl2(2,4) |
| 187 | O—CO—NH—C3H7(i) | 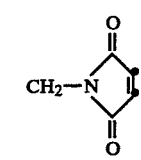 |
| 188 | O—CO—NH—C4H9(n) | CH2—CH2—N—(C2H5)2 |

TABLE IX (Ar = 5-membered heterocycle with R28, Z3); m = O

| Compound | Z3 | R28 | X | Q |
|---|---|---|---|---|
| 189 | S | H | CN | CH2—O—C6H5 |
| 190 | S | H | Cl | CH2-N(maleimide) |
| 191 | S | H | CN | CH2—CH2—OH |
| 192 | S | H | CN | CH2—CH2—O—CO—NH—CH3 |
| 193 | S | Cl | CN | CH2—O—C2H3—(CH3)2—(2,3) |
| 194 | S | Cl | CH3 | CH2—O—C6H4—Cl(4) |
| 195 | O | Cl | CN | CH2—CH2—OH |
| 196 | O | Cl | CH3 | CH2—CH2—OH |
| 197 | O | Cl | Cl | 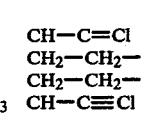 |
| 198 | O | H | CN | CH2—CH2—OH |
| 199 | O | H | CN | CH2—CH2—O—CO—NH—CH3 |
| 200 | O | H | CH3 | CH2—CH2—OH |
| 201 | O | H | CH3 | CH2—CH2—O—CO—NH—C6H5 |
| 202 | O | H | Cl | CH2-N(maleimide) |
| 203 | O | H | CN | CH=C=Cl |
| 204 | N—CH3 | H | CN | CH2—CH2—OH |
| 205 | N—CH3 | H | CN | CH2—CH2—O—CO—C2H5 |
| 206 | N—CH3 | H | CH3 | CH—C≡Cl |

TABLE IX-continued (Ar = 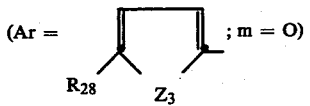 ; m = O)

| Compound | $Z_3$ | $R_{28}$ | X | Q |
|---|---|---|---|---|
| 207 | S | Cl | CN | 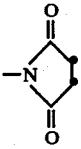 |
| 208 | S | Cl | CN | 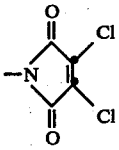 |

FORMULATION EXAMPLES

EXAMPLE 4

Dusts

The following substances are used to formulate
(a) 5% and (b) a 2% dust:
(a)
  5 parts of active substance
  95 parts of talc;
(b)
  2 parts of active substance
  1 part of highly dispersed silicic acid
  97 parts of talc.

The active substances are mixed with the carriers and ground and in this form can be processed to dusts for application.

EXAMPLE 5

Granulate

The following substances are used to formulate a 5% granulate:
  5—parts of active substance
  0.25—part of epichlorohydrin
  0.25—part of cetyl polyglycol ether
  3.25—parts of polyethylene glycol
  91—parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

EXAMPLE 6

Wettable Powders

The following constituents are used to formulate (a) a 70%, (b) a 40%, (c) and (d) a 25% and (e) a 10% wettable powder:
(a)
  70 parts of active substance
  5 parts of sodium dibutylnaphthylsulfonate
  3 parts of naphthalenesulfonic acid/phenolsulfonic acid/formaldehyde condensate (3:2:1)
  10 parts of kaolin
  12 parts of Champagne chalk
(b)
  40 parts of active substance
  5 parts of sodium ligninsulfonate
  1 part of sodium dibutylnaphthalenesulfonic acid
  54 parts of silicic acid
(c)
  25 parts of active substance
  4.5 parts of calcium ligninsulfate
  1.9 parts of Champagne chalk/hydroxyethyl cellulose mixture (1:1)
  1.5 parts of sodium dibutylnaphthalenesulfonate
  19.5 parts of silicic acid
  19.5 parts of Champagne chalk
  28.1 parts of kaolin
(d)
  25 parts of active substance
  2.5 parts of isooctylphenoxy-polyethylene-ethanol
  1.7 parts of a Champagne chalk/hydroxyethyl cellulose mixture (1:1)
  8.3 parts of sodium aluminium silicate
  16.5 parts of kieselguhr
  46 parts of kaolin
(e)
  10 parts of active substance
  3 parts of a mixture of the sodium salts of saturated fatty alcohol sulfates
  5 parts of naphthalenesulfonic acid/formaldehyde condensate
  82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants.

EXAMPLE 7

Emulsifiable concentrate

The following substances are used to formulate a 25% emulsifiable concentrate:
  25—parts of active substance
  2.5—parts of epoxidised vegetable oil
  10—parts of an alkylarylsulfonate/fatty alcohol polyglycol ether mixture
  5—parts of dimethyl formamide
  57.5—parts of xylene.

By diluting such a concentrate with water it is possible to prepare emulsions of the desired concentration, which are especially suitable for leaf application.

BIOLOGICAL EXAMPLES

EXAMPLE 8

Pre-emergence antidote test (basic test)

General test method

Small flower pots (diameter 6 cm at the top) are filled with garden soil into which the plant seed is sown, covered with the soil and gently pressed firm. Then the antidote is sprayed as test substance in the form of a dilute solution (obtained from a wettable powder) in an amount corresponding to 4 kg/ha. The herbicide is sprayed onto the soil directly afterwards in corresponding amount. After the pots have stood for 18 days at about 20°–23° C. and 60°–70° C. relative humidity, evaluation is made in accordance with a linear scale from 1 (denoting total damage to the plant) to 9 (denoting undamaged healthy plant). Plants without antidote protection are used as control.

The following herbicides and plants were employed:
(1) 1.5 kg/ha of α-[4-(p-trifluoromethylphenoxy)-phenoxy]-propionic acid n-butoxyethyl ester in maize of the "Orla 264" variety.
(2) 1.5 kg/ha of Metolachlor=N-(-1-methyl-2-methoxyethyl)-N-chloroacetyl-2-ethyl-6-methylaniline in sorghum of the "Funk G-522" variety.
(3) 2 kg/ha of Prometryn=2,4-bis(isopropylamino)-6-methylthio-s-triazine in soybeans.
(4) 2 kg/ha of 4-ethylamino-6-tert-butylamino-2-chloro-s-triazine in wheat of the "Farnese" variety.
(5) 4 kg/ha of Prometryn=2,4-bis(isopropylamino)-6-methylthio-s-triazine in sorghum of the "Funk G-522" variety.
(6) 2 kg/ha of α-[4-p-trifluoromethylphenoxy)-phenoxy]-propionic acid n-butoxyethyl ester in barley of the "Mazurka" variety.

In these tests, the antidote action was e.g. as follows:

| Test variant | Compound | Rating of the herbicidal action (without/with antidote) |
|---|---|---|
| 2 | 2 | 4/6 |
| 2 | 76 | 3/9 |
| 2 | 77 | 3/9 |
| 3 | 5 | 2/6 |
| 4 | 23 | 4/7 |
| 5 | 15 | 3/7 |

EXAMPLE 9

Antidote action on separate application (antidote/pre-emergence, herbicide/post-emergence)

General test method

Small flower pots (diameter 6 cm at the top) are filled with sandy loam into which the plant is sown. After covering the seed, a dilute solution of the antidote as test substance is sprayed onto the surface of the soil in an amount corresponding to 4 kg/ha. The pots are kept at 20°–23° C. and 60°–70° C. relative humidity. When the plants have attained the 2- to 3-leaf stage after 10 days, they are treated as indicated below with the corresponding amount of herbicide. Evaluation is made 14 days after the application of the herbicide, using the same rating system as in Example 8. Plants unprotected by antidote are used as control.

The herbicides and plants employed are:
(1) 4 kg/ha of Ametryn=2-ethylamino-4-isopropylamino-6-methylthio-s-triazine in maize of the "Orla 264" variety.
(2) 1 kg/ha of Prometryn=2,4-bis(isopropylamino)-6-methylthio-s-triazine in sorghum of the "Funk G-522" variety.
(3) 0.25 kg/ha of α-[4-(p-trifluoromethylphenoxy)-phenoxy]-propionic acid n-butoxyethyl ester in barley of the "Mazurka" variety.

A good antidote action was obtained in these tests with compounds of the formula (I). A rating of 2/6 was obtained in test variant 2 with compound 84.

EXAMPLE 10

Antidote action in transplanted rice on separate application (antidote/pre-emergence, herbicide/post-emergence)

Plastic tubs measuring 8×8×10 cm are filled with wet marshy soil to 2 cm below the edge. A dilute solution of the antidote as test substance is sprayed onto the surface of the soil in an amount corresponding to 4 kg/ha. Rice plants of the "IR-88" variety are transplanted in the 1½- to 2-leaf stage into the prepared tubs. On the next day, the water level is raised to about 1.5 cm. Four days after transplantation, 2-ethylamino-4-(1,2-dimethyl-n-propylamino)-6-methylthio-s-triazine is added to the water in granule form in an amount corresponding to 0.75 kg/ha. During the test, the temperature is 26°–28° C. and the relative humidity 60°–80° C. Evaluation is made 20 days after the treatment with herbicide, using the same rating as in Example 8, Plants not protected with antidote are used as control. In this test, compounds 2, 9 and 79 reduced the rating 4 of the herbicidal action to 8, 8 and 7 respectively of the antidote.

EXAMPLE 11

Pre-emergence antidote test in nutrient solution

A Hewitt nutrient solution, which contains the amount of herbicide indicated below as well as 10 ppm of the antidote to be tested, is prepared.

Seeds which would normally be damaged in the indicated test concentrations of the herbicide employed are sown in granular zonolith (expanded vermiculite) in plastic flower pots (diameter 6 cm at the top) which are perforated at the bottom. Each pot is then placed in a second transparent plastic flower pot (diameter 7 cm at the top) which contains about 50 ml of the nutrient solution prepared with herbicide and antidote. This nutrient solution then rises by capillary action in the filling material of the smaller pot and moistens the seed and the germinating plant. The loss in fluid is daily replenished to 50 ml with pure Hewitt nutrient solution. Evaluation is made 3 weeks after the start of the test, using the same rating as in Example 8. The control solution employed in the parallel test contains no antidote.

The herbicides and plants employed are:
(1) 4 ppm of Prometryn=2,4-bis(isopropylamino)-6-methylthio-s-triazine in sorghum of the "Funk G-522" variety.
(2) 4 ppm of 4-ethylamino-6-tert-butylamino-2-chloro-s-triazine in wheat of the "Farnese" variety.
(3) 4 ppm of α-[4-(p-trifluoromethylphenoxy)-phenoxy]-propionic acid n-butoxyethyl ester in barley of the "Mazurka" variety.
(4) 5 ppm of Metolachlor=N-(1-methyl-2-methoxyethyl)-N-chloroacetyl-2-ethyl-6-methaniline in sorghum of the "Funk G-522" variety.

The antidote action obtained in these tests is e.g. as follows:

| Test variant | Compound | Rating of the herbicidal action without/with antidote |
|---|---|---|
| 2 | 23 | 4/7 |
| 2 | 78 | 3/6 |
| 4 | 23 | 4/7 |

-continued

| Test variant | Compound | Rating of the herbicidal action without/with antidote |
|---|---|---|
| 5 | 82 | 1/6 |

EXAMPLE 12

Pre-emergence antidote test in nutrient solution (rice)

A Hewitt nutrient solution, which additionally contains 10 ppm of the antidote to be tested, is prepared.

Rice seeds of the "IR-8" variety are sown in granular filling material (granular zonolith) in plastic flower pots (diameter 6 cm at the top) which are perforated at the bottom. Each pot is then placed in a second transparent plastic flower pot (diameter 7 cm at the top) which contains about 50 ml of the nutrient solution prepared from herbicide and antidote. This nutrient solution then rises by capillary action in the filling material of the smaller pot and moistens seed and plant. The loss in fluid is daily replenished to 50 ml with pure Hewitt solution. After 15 days, the rice plants are transplanted in the 2- to 2½-leaf stage in rectangular plastic pots (8=8=10 cm) which are filled with 500 ml of wet, marshy soil. The water level is increased next day to 1-2 cm above the level of the soil. Four days after transplantation, the herbicide 2-ethylamino-4-(1,2-dimethyl-n-propylamino)-6-methylthio-s-triazine is added in granule form in an amount corresponding to 0.75 kg/ha. Evaluation is made 3 weeks later in accordance with the rating employed in Example 8 and subsequent Examples. The control solution used in the parallel test contains no antidote. A good antidote action was obtained in this test with the compounds of the formula (I), in particular with compounds 2, 9, 79 and 81.

EXAMPLE 13

Post-emergence antidote test in nutrient solution

General test method

Small plastic flower pots (diameter 6 cm at the top), which are perforated at the bottom, are filled with granular zonolith and the seeds are sown in this material. Each pot is then placed in a second transparent plastic flower pot (diameter 7 cm at the top) which contains 50 ml of water which rises by capillary action and moistens the seed. From the 5th day, the continual loss in water is made up with Hewitt nutrient solution. From the 15th day, when the plant is in the 1½-2-leaf stage, 10 ppm of the antidote to be tested and the amount of herbicide indicated below are added to the nutrient solution which has again been replenished to 50 ml. From the 16th day, the loss in fluid is again made up with pure Hewitt nutrient solution. During the entire duration of the test, the temperature is 20°-23° C. and the relative humidity 60°-70° C. Evaluation is made 3 weeks after the addition of the herbicide in accordance with the rating employed in Example 8 and subsequent Examples.

Test variants (1) 15 ppm of α-[4-(3,5-dichloropyridyl-2-oxy)-phenoxy]-propionic acid propargylthiolo-ester in wheat of the "Zenith" variety.

(2) 4 ppm of 4-ethylamino-6-tert-butylamino-2-chloro-s-triazine in wheat of the "Zenith" variety.

(3) 2 ppm of α-[4-(p-trifluoromethylphenoxy)-phenoxy]-propionic acid n-butoxyethyl ester in maize of the "Orla" variety.

(4) 8 ppm of α-[4-(p-trifluoromethylphenoxy)-phenoxy]-propionic acid n-butoxyethyl ester in sorghum of the "Funk G-522" variety.

(5) 4 ppm of Prometryn =2,4-bis(isopropylamino)-6-methylthio-s-triazine in sorghum of the "Funk G-522" variety.

(6) 8 ppm of α-[4-(3,5-dichloropyridyl-2-oxy)-phenoxy]-propionic acid methyl ester in wheat of the "Zenith" variety.

A good antidote action is obtained in these tests with compounds of the formula (I). The results are as follows:

| Test variant | Compound | Rating of the herbicidal influence without/with antidote |
|---|---|---|
| 1 | 5 | 4/7 |
| 2 | 23 | 4/7 |
| 2 | 78 | 3/6 |

Example 14

Antidote test - seed soaking

Rice seeds of the "IR-8" variety are immersed for 48 hours in solutions of the test substances in concentrations of 10, 100 or 1000 ppm. The seeds are then allowed to dry for about 2 hours until they are no longer tacky. Rectangular plastic tubs (8×8×10 cm) are filled with sandy loam to 2 cm below the edge. 4 g of seeds are sown in each tub and only very loosely covered (to about the diameter of the seed). The soil is kept in a moist (non-marshy) state. Then a dilute solution of the herbicide N-(1-methyl-2-methoxyethyl)-N-chloroacetyl-2-ethyl-6-methylaniline is applied in an amount corresponding to 1.5 kg/ha. Evaluation is made 7 and 18 days after transplantation in accordance with the rating employed in Example 8 and subsequent Examples. A good antidote action is obtained in this test with compounds of the formula (I), in particular with compounds 9 (3/6), 80 (3/6), 155 (2/6), 157 (2/6) and 41 (2/6).

Example 15

Antidote test (root dipping)

Rice plants of the "IR-8" variety are reared in soil until they are in the 1½- to 2-leaf stage and then superficially washed. Then only the roots of the plants, in bunches, are dipped for 45 minutes in a dish containing solutions of the test substance in a concentration of 10, 100 or 1000 ppm. The plants are then transplanted in sandy loam in containers measuring 47×29×24 cm. The surface of the soil is covered with water to a height of 1½ to 2 cm. One day after transplantation, a dilute solution of the herbicide N-n-propoxyethyl-N-chloroacetyl-2,6-diethylaniline is pipetted directly into the water in an amount corresponding to 1.5 kg/ha. Evaluation is made 7 and 18 days after transplantation in accordance with the rating employed in Example 8 and subsequent Examples. Good antidote action is obtained in this test with compounds of the formula (I).

What is claimed is:

1. A compound of the formula

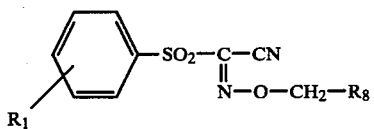

wherein
R₁ is hydrogen or halogen, and

R₈ is phthalimido, 4,5,6,7-tetrahydrophthalimido or 3a,4,7,7a-tetrahydrophthalimido attached at the nitrogen atom to the remainder of the molecule.

2. A compound according to claim 1 in which R₁ is hydrogen and R₈ is phthalimido.

3. An antidote composition for use in safening plants against the harmful effects of potent herbicides which comprises (1) an antidotally effective amount of a compound according to claim 1 and (2) an inert carrier.

* * * * *

UNITED STATES PATENT AND TRADEMARK OFFICE
CERTIFICATE OF CORRECTION

PATENT NO. : 4,439,230

DATED : March 27, 1984

INVENTOR(S) : Werner Fory, Henry Martin, and Georg Pissiotas

It is certified that error appears in the above-identified patent and that said Letters Patent is hereby corrected as shown below:

On the cover page, Item 62, Line 2 should read--

4,353,735 --.

Signed and Sealed this

Twenty-second Day of October 1985

[SEAL]

Attest:

DONALD J. QUIGG

Attesting Officer

Commissioner of Patents and Trademarks—Designate